N. B. SALERNI

VAGINAL SYRINGE

April 14, 1931.

Re. 18,049

Original Filed July 26, 1929

INVENTOR,
Nicholas B. Salerni
By Minturn & Minturn,
Attorneys.

Reissued Apr. 14, 1931

Re. 18,049

UNITED STATES PATENT OFFICE

NICHOLAS B. SALERNI, OF INDIANAPOLIS, INDIANA

VAGINAL SYRINGE

Original No. 1,761,588, dated June 3, 1930, Serial No. 381,194, filed July 26, 1929. Application for reissue filed December 11, 1930. Serial No. 501,735.

This invention relates to vaginal syringes of the type adapted for use in irrigating and distending the vagina for treating irritated and diseased tissue therein.

The primary purposes of the invention are to provide a syringe of the correct anatomical form in combination with means incorporated therewith for sealing the vagina to prevent escape of irrigating fluids therearound; to provide means in the syringe for regulating and shutting off the flow and discharge of the liquid to and from the vagina; to provide a syringe easily taken apart for cleaning; to provide a syringe having a regulatable discharge that will not clog up; and to provide a removable spray tip.

Figure 1:
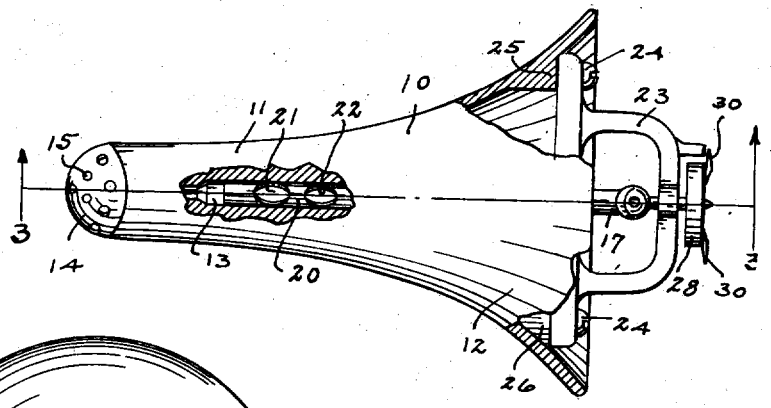
Figure 2:
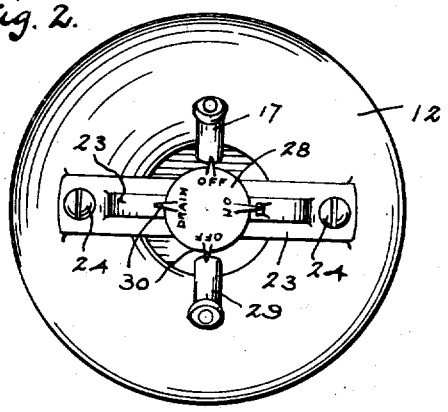

These and other objects will become apparent in the following description of the invention as illustrated by the accompanying drawing, in which Fig. 1 is a top plan view of a syringe embodying the invention with parts broken away to disclose the inner construction;

Fig. 2, a rear elevation; and

Figure 3:
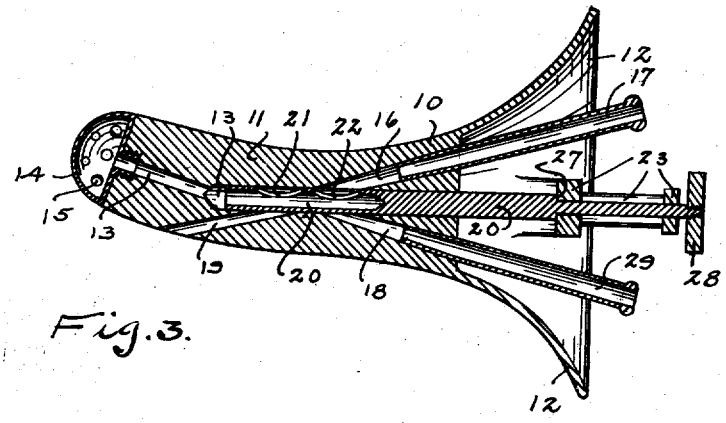

Fig. 3, a vertical longitudinal section on the line 3—3 in Fig. 1.

Like characters of reference indicate like parts throughout the several views in the drawing.

I form a syringe body 10 to have the nozzle 11 and the rear, outwardly flaring, conical flange 12. The nozzle 11 has a central passage 13 formed therethrough entering from without the rear end of the nozzle within the flange 12. The passage 13 is continued to discharge from the forward end of the nozzle, and a tip 14 is screw-threadedly engaged in the passage to form a smooth rounded end over the nozzle. The tip 14 is hollow and is provided with a plurality of holes 15 therethrough to permit discharge through the tip from the passage 13 therebehind.

An inlet passage 16 is formed in the rear end of the nozzle 11 to extend diagonally toward the central passage 13, and is tapered slightly to a larger diameter at its orifice at the rear of the nozzle to receive and frictionally retain therein the tube 17 which has a bulb outer end to receive thereover a rubber tube (not shown).

Similarly, a discharge passage 18 is carried diagonally in from the rear face of the nozzle 11 to communicate with the passage 13 and has its rear portion tapered to receive and frictionally retain therein the tube 29, over the outer bulb end of which may also be slipped a rubber tube (not shown). A passage 19 is formed in the under side of the nozzle 11 to enter therein near the tip 14 and extend diagonally toward and communicate with the passage 13. There are thus three orifices about the passage 13, one from the inlet passage 16 on the upper side and two on the lower side, one from the discharge passage 18 and one from the forward passage 19.

A stem 20 is carried in the passage 13 with a sliding fit so that it may be revolved about its axis therein. The forward end of the stem 20 is hollow and has two orifices 21 and 22 positioned along one side through which communication may be had to the interior of the stem. The orifices of the above indicated passages and the orifices 21 and 22 are so located that upon rotating the stem 20, the orifice 22 may register with the orifice of the inlet passage 16 whereby there is then produced a continuous passage through the inlet passage 16, through the steam 20 and out the passage 13 through the tip 14. The orifices of the other two passages 18 and 19 are then closed. By rotating the stem ninety degrees, all passage orifices are closed and there may be neither inlet nor discharge through the tip 14 or passage 19.

Rotating the stem ninety degrees further closes the orifice of the passage 16 and registers the orifices 21 and 22 with the orifices of the passages 18 and 19 affording a continuous discharge passage from near the forward end of the nozzle without employing the small holes of the tip 14 therefor out through the tube 29 to permit large particles of mucus and the like to pass therethrough.

The stem 20 is retained in the passage 13 by the handle 23 which is detachably carried diametrically across the flange 12, the screws 24 being passed through the ends of the handle and screw-threadedly entered into the shoulders 25, 26. The stem 20 has an outer end of reduced diameter rotatably passing through the handle with a shoulder 27 contacting the forward side of the handle. A disc 28 is screw-threadedly fixed to the outer end of the stem and serves as a means for rotating the stem. Indicating points 30 are provided to indicate the position of the stem orifices relative to the passage orifices.

The operation of the syringe is evident from the foregoing description. The flange 12 forms an annular seal at the outer end of the vagina and suitable medicated liquid is supplied under pressure through the tube 17, by suitable rotation of the stem 20 as above indicated. The liquid may be sprayed from the tip 14 and then shut off to permit retention for a desired interval, following which the stem may be further rotated to permit discharge of the liquid from the tube 29. By removing the handle 23, the stem 20 may be withdrawn from the passage. The tip 14 may be removed and the tubes 17 and 29 pulled out, all for the purposes of complete sterilization.

Having thus shown and described the invention in the one form now best known to me, it being obvious that structural changes may be made in that form without departing from the spirit of the invention, I do not desire to be limited to that precise form, nor any more than may be necessitated by the following claims.

I claim:

1. In a vaginal syringe, a nozzle, an outwardly, rearwardly extending flange on the rear of the nozzle, said nozzle having a passage longitudinally disposed therein and an inlet passage communicating with the first passage, and a stem rotatably carried to intercept selectively communication between said first passage and said inlet passage.

2. In a vaginal syringe, a nozzle, an outwardly, rearwardly extending flange on the rear of the nozzle, said nozzle having a passage longitudinally disposed therein and an inlet passage communicating with the first passage, and a stem rotatably carried to intercept selectively communication between said first passage and said inlet passage, said nozzle having a discharge passage communicating with said first passage and selectively intercepted by said stem.

3. In a vaginal syringe, a nozzle, an outwardly, rearwardly extending flange on the rear of the nozzle, said nozzle having a passage longitudinally disposed therein and an inlet passage communicating with the first passage, and a stem rotatably carried to intercept selectively communication between said first passage, and said inlet passage, said nozzle having a discharge passage communicating with said first passage and selectively intercepted by said stem, said nozzle having an under passage entering from near the forward end of the nozzle and discharging into said first passage to be intercepted selectively by said stem.

4. In a vaginal syringe, a nozzle, an outwardly, rearwardly extending flange on the rear of the nozzle, said nozzle having a passage longitudinally disposed therein and an inlet passage communicating with the first passage, and a stem rotatably carried to intercept selectively communication between said first passage and said inlet passage, said nozzle having a discharge passage communicating with said first passage and selectively intercepted by said stem, said nozzle having an under passage entering from near the forward end of the nozzle and discharging into said first passage to be intercepted selectively by said stem, and a spray tip on the forward end of said nozzle in communication with said first passage.

5. In a vaginal syringe, a nozzle, an outwardly, rearwardly extending flange on the rear of the nozzle, said nozzle having a passage longitudinally disposed therein and an inlet passage communicating with the first passage, and a stem rotatably carried to intercept selectively communication between said first passage and said inlet passage, said nozzle having a discharge passage communicating with said first passage and selectively intercepted by said stem, said nozzle having an under passage entering from near the forward end of the nozzle and discharging into said first passage to be intercepted selectively by said stem, and means removably retaining said stem in said nozzle.

6. In a vaginal syringe, a nozzle, a flange extending rearwardly and outwardly from the nozzle, said nozzle having a central passage longitudinally therethrough and an inlet and a discharge passage, and valve means selectively intercepting said passages.

7. In a vaginal syringe, a nozzle, a flange extending rearwardly and outwardly from the nozzle, said nozzle having a central passage longitudinally therethrough and an inlet and a discharge passage, and valve means selectively intercepting said passages, and said nozzle having an under passage communicating from without with the said central passage, said valve means being adapted to interconnect said discharge passage and said under passage.

8. In a vaginal syringe, a nozzle, a flange extending rearwardly and outwardly from the nozzle, said nozzle having a central passage longitudinally therethrough and an inlet and a discharge passage, and valve means selectively intercepting said passages, and said nozzle having an under passage communicating from without the said central passage, said valve means being adapted to interconnect said discharge passage and said under passage, and a spray tip removably secured on the forward end of the nozzle in communication with said central passage.

9. In a vaginal syringe, a nozzle, a central passage therethrough, a valve in said passage, and a handle removably retaining the valve.

10. In a vaginal syringe, a nozzle, a central passage therethrough, a valve in said passage, and a handle removably retaining the valve, an inlet tube, and a discharge tube, both of said tubes being in communication with said passage.

11. In an irrigating device, a nozzle having a central passage discharging from the forward end thereof and an inlet and a rear discharge passage each communicating with the central passage, said nozzle having a second inlet passage extending from an orifice near the front discharge end thereof and communicating with said central passage, and valve means comprising a hollow stem in said central passage having side inlets selectively intercepting said inlet and discharge passages.

12. In a syringe for irrigation within the human body, a nozzle having a central passage therein normally discharging from the front end of the nozzle and having inlet and discharge passages normally communicating with said central passage, and a hollow stem having side inlets adapted to be rotatively moved to intercept selectively said inlet and discharge passages, and said nozzle having a second inlet passage near its forward end, whereby by movement of the stem, the selection of a continuous flow may be had from said first inlet passage and out the forward end of the nozzle with no flow from the second inlet passage out through the discharge passage, a flow from through the said second inlet passage out through the discharge passage without a flow from the first inlet passage, and of no flow through either the said first inlet passage and the discharge passage.

NICHOLAS B. SALERNI.